United States Patent
Kishigami

[11] Patent Number: 6,059,571
[45] Date of Patent: May 9, 2000

[54] METHOD FOR EMBEDDING MARK IN DENTURE AND IMPLEMENT FOR MAKING RECESS USED THEREFOR

[76] Inventor: Hisashi Kishigami, 2-25-21, Shimizugaoka, Sumiyoshi-ku, Osaka, Japan

[21] Appl. No.: 09/183,216

[22] Filed: Oct. 27, 1998

[30] Foreign Application Priority Data

Mar. 14, 1998 [JP] Japan .................................. 10-106873

[51] Int. Cl.⁷ ..................................... A61C 13/00
[52] U.S. Cl. ........................... 433/167; 433/171; 433/229
[58] Field of Search ..................... 433/167, 171, 433/215, 229, 6

[56] References Cited

U.S. PATENT DOCUMENTS

| | | | |
|---|---|---|---|
| 3,503,127 | 3/1970 | Kasdin et al. | 433/229 X |
| 4,208,795 | 6/1980 | Muhlemann et al. | 433/229 X |
| 4,571,739 | 2/1986 | Resnick | 433/167 X |
| 5,078,153 | 1/1992 | Nordlander et al. | 433/215 X |
| 5,326,349 | 7/1994 | Baraff | 433/167 X |

*Primary Examiner*—Nicholas D. Lucchesi

[57] ABSTRACT

In order to solve such problem that heating a mark such as a one-chip microprocessor which is easily damaged thermally in case of curing a heat-curing resin enclosing such one-chip microprocessor could have not been essentially made in event of embedding sealably such mark in the resin section of a denture, the present invention is characterized by that a groove-shaped recess for inserting the mark has previously been defined in a wax pattern indispensable for fabrication of the denture. For defining such recess, the implement for making a recess for embedding sealably the mark which is provided with a head shaped so as to have substantially the same dimension as that of the mark is used. More specifically, the head of the implement which has been heated by hot water is pressed upon a surface of the wax pattern to define such a groove-shaped recess as a result of melting a portion of the wax thus heated. Then, a heat-curing resin is poured into the recess defined in the wax pattern, whereby a cured resin section containing the recess is shaped. Thereafter the mark is inserted into the groove-shaped recess, and then a gap defined around the mark and an exposed portion of the mark is covered with a resin used for direct restoration which cures instantly at ordinary temperatures, or a photo-polymerizing resin to sealably embed the gap and the exposed part of the mark. When a one-chip microprocessor transmitting identification number us utilized as a mark and is embedded in the resin section of such denture, the resulting denture can be identified simply and positively. As a result, management for dentures becomes very easy un dentist's or dental mechanic's office.

1 Claim, 2 Drawing Sheets

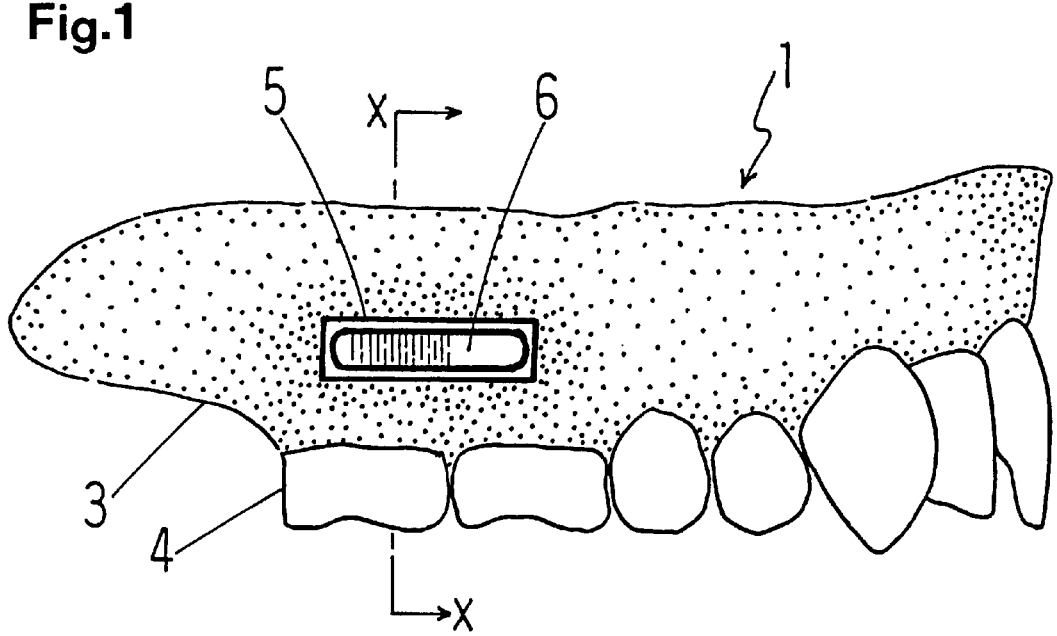
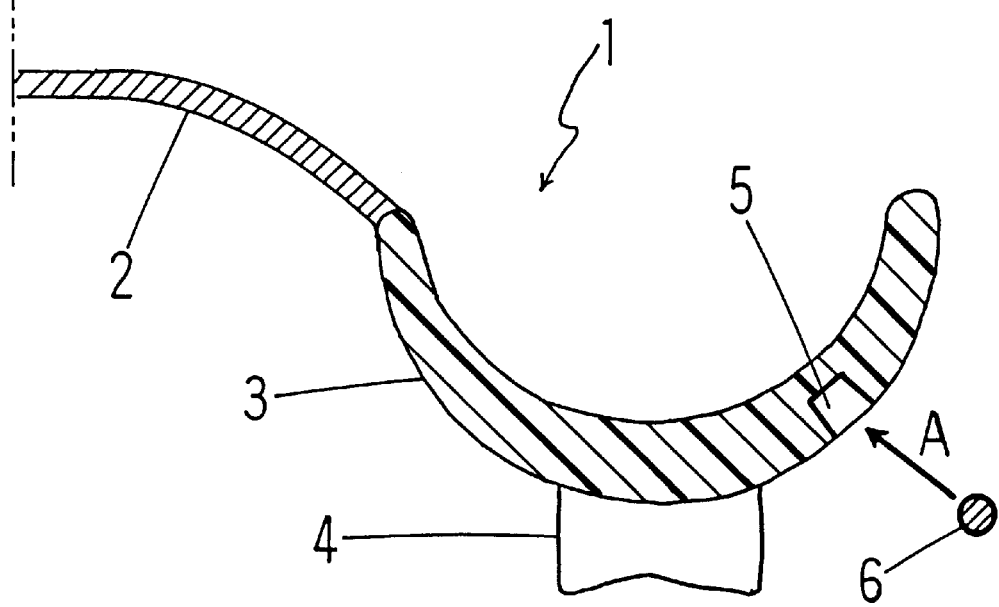

METHOD FOR EMBEDDING MARK IN DENTURE AND IMPLEMENT FOR MAKING RECESS USED THEREFOR

BACKGROUND OF THE INVENTION

1. Field of the Invention

The present invention relates to a denture capable of identifying its owner wherein a mark such as a one-chip microprocessor is embedded sealably in a resin layer of the denture, whereby one's identity who puts on such denture may be confirmed, and at the same time, the denture itself can be easily and positively identified in dental office or nursing facilities for old people as well as to an implement for making recess for sealably embedding such mark used for fabrication of the novel denture.

2. Description of the Related Art

As an identifying means of individual for confirming his (or her) personal identity, such a manner that a large tooth such as cheek tooth or an artificial tooth made of ceramics implanted in a denture is bored by means of a drill for dental use, a mark such as one-chip microprocessor is inserted into the cavity thus bored, and then the mark held in the cavity is sealed with a photopolymerizing resin has heretofore been applied. However although practical utility as to effect for confirming one's identity has been appreciated by embedding sealably a mark contained in a cavity or a recess, there is such a disadvantage that cracks appear on the artificial tooth thus bored, and it results in damage of the tooth in case of denture, whereby strength of such artificial tooth reduces remarkably. For this reason, it is not practiced to embed sealably a mark in a recess bored in an artificial tooth of a denture for confirming one's identity who puts on such denture under the existing circumstances.

On one hand, it is required in a dental office to correctly hold each date of fabrication in a large number of dentures as well as names of dental mechanics who fabricate such dentures. Particularly, there is a possibility of troubles in medical care in the case where one patient has a plurality of dentures, if all the dentures are not positively identified.

Furthermore, in facilities such as a senior citizens' home in which a number of old people are received, it is taken usually such a procedure that all the dentures are collected from their owners after each meal, and then the dentures are washed all together. In such case, it is inevitable to identify all the dentures to give back to their correct owners without any mistake.

Because of such situation, some dentists have engraved heretofore a name or a number, a symbol or the like for identification of a certain owner on the surface of a resin or a metal base in his (or her) denture. However, it is difficult to decipher such engraved characters or the like, besides there is such a possibility that recesses for the characters or the like become a source for giving out a bad smell. There is also such a disadvantage that it becomes impossible to decipher such engraved characters, after they had been worn away as a result of utilization of the denture for a long period of time.

OBJECTS AND SUMMARY OF THE INVENTION

The present invention has been made in view of the problems as described above involved in the prior art. Accordingly, an object of the present invention is to provide a denture capable of easily and positively identifying its owner without boring any cavity on any artificial tooth implanted in the denture or without engraving any character or symbol on a resin plate of the denture.

Another object of the present invention is to provide an implement for making easily recess for sealably embedding a mark used for fabrication of a novel denture capable of identifying its owner.

In order to achieve the above described objects, the present inventor has considered that an artificial tooth of denture must be avoided as a site in which a mark to be embedded sealably, because such artificial tooth causes easily deterioration of strength due to making a recess for embedding sealably such mark, but an artificial gingival section in which a resin layer is thickened should be selected. On the other hand, the present inventor has taken notice of one-chip microprocessor being an embedding type electronic responser which is going to spread for identifying animal individual as a mark to be embedded in a denture.

In this connection, however, one-chip microprocessor is easily damaged by heat, since it contains an electonic circuit in a glass capsule. Thus, such one-chip microprocessor cannot be directly introduced into a heat-curing resin which is to be cured by means of boiling water contained in flask. Under the circumstances, the present inventor has repeated a number of experiments to find a manner for embedding sealably such one-chip microprocessor into a resin layer of denture without heating the one-chip microprocessor. As a result of eager study by the inventor, the present invention has been completed finally.

More specifically, in the case when a dentist gets a tooth form from a patient and prepares a wax pattern based on the tooth form thus obtained, a groove-shaped recess for holding a mark such as a one-chip microprocessor has been previously formed on an artificial gingival section made of such solidified wax pattern by the use of the implement for making recess for sealably embedding a mark used for fabrication of a denture according to the present invention. Then, the wax pattern on which has been defined such groove-shaped recess is contained in a flask, a heat-curing resin is poured into a gap defined in the wax pattern, and the resin thus poured is cured thermally. As a result, a groove-shaped recess for holding a mark is defined on such cured resin layer having a thicker thickness, whereby the mark such as a one-chip microprocessor may be tightly held in the recess. Thereafter, when the mark contained in the recess is covered with a resin used for direct restoration which cures instantly at ordinary temperatures, a photo-polymerizing resin, or the like resin, the mark of one-chip microprocessor can be easily embedded and sealed in the resin layer of a denture.

In the denture capable of identifying its owner which has been fabricated in accordance with the above described manner, the mark is embedded and sealed in the resin layer of artificial gingival section having a thicker thickness. Thus, there is no need of boring an artificial tooth of denture, resulting in no fear of reducing strength of the denture fabricated. On one hand, a registered number of the one-chip microprocessor embedded and sealed in the denture as a mark can be read out instantly by the use of a reader. Accordingly, when such reader is allowed to simply come near the denture, owner of the denture can be easily and positively identified.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 1 is a side view showing an embodiment of the denture according to the present invention;

FIG. 2 is a schematic sectional view taken along the line X X of FIG. 1; and

DETAILED DESCRIPTION OF THE PREFERRED EMBODIMENTS

Figure 3:
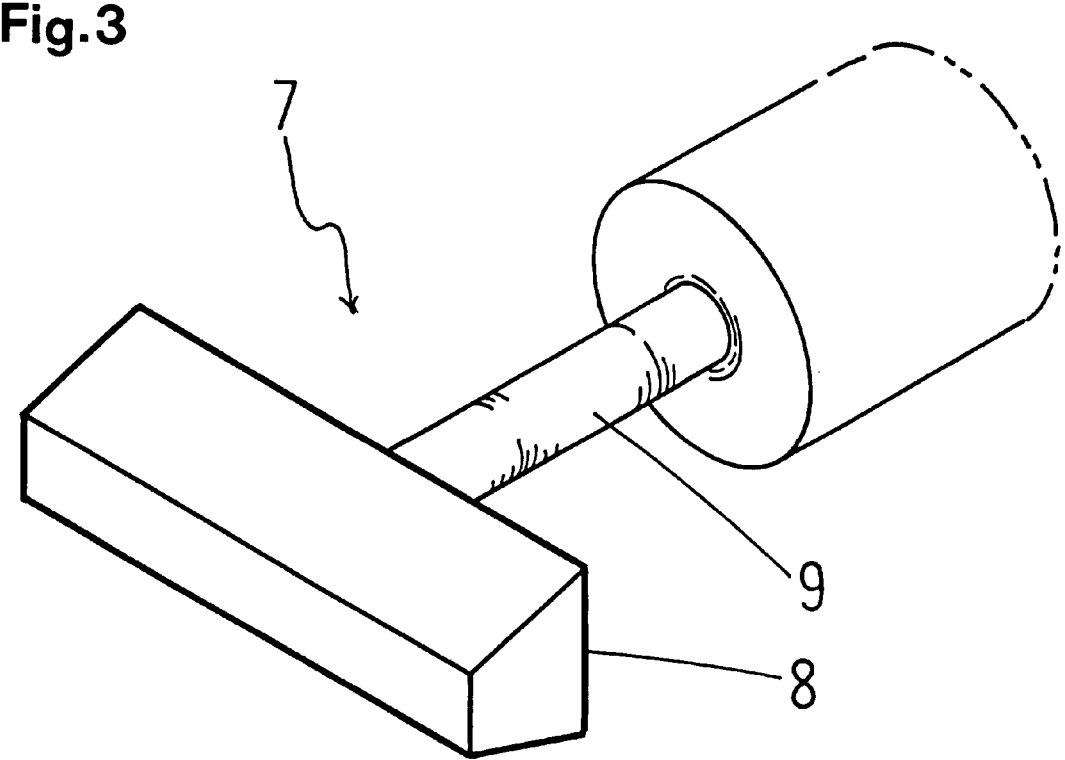
FIG. 3 is a perspective view showing an embodiment of the implement for making a recess for embedding sealably a mark in resin layer of a denture.

Referring to FIGS. 1 and 2 each illustrating an embodiment of the denture 1 capable of identifying its owner according to the present invention wherein a groove-shaped recess has been previously defined on a resin layer of an artificial gingival section 3 thereof as a groove 5 for holding a mark 6 such as a one-chip microprocessor to sealably embed the same therein. More specifically, a recess is defined in the case when a wax pattern is fabricated in a dental mechanic's office on the basis of a patient's tooth form acquired in a dental office as the groove 5 for holding such mark on the wax pattern at a site where the resin layer of the artificial gingival section 3 in the vicinity of an artificial molar tooth 4 becomes thicker.

In case of defining the above described groove 5 for holding a mark, it is convenient to employ an exclusive implement 7 for making a recess used for embedding sealably a mark shown in FIG. 3.

Referring to FIG. 3, the implement 7 for making a recess used for embedding sealably a mark composed of a head 8 shaped so as to have substantially the same dimension as that of the mark 6 of one-chip microprocessor or the like to be sealably embedded, and a grip 9 to the extreme end of which is attached the aforesaid head 8 is shown. First, the head 8 of the implement 7 for making a recess used for embedding sealably a mark is immersed in water warmed at about 40° C., and the head thus warmed is forcibly pressed on a wax pattern. As a result, the paraffin wax solidified compactedly is softened locally, whereby a recess having slightly larger size than that of the mark can be defined without damaging the wax pattern. In this case, however, there is a fear of deforming the wax pattern, if the head is warmed excessively, then the wax melts easily. Therefore, temperature of warmed water should be carefully adjusted. Alternatively, a groove-shaped recess may be defined on a wax pattern by scraping off the wax into a contour corresponding roughly to a required recess by the use of denturist's knife. Then, the head 8 of the above described implement 7 for making recess used for embedding sealably a mark is forcibly inserted into the contour of the above described tentative recess, so that a finished groove 5 for holding mark into which such a target mark is contained tightly can easily be defined. In any case, it is very easy working for dental mechanic to define such groove 5 for holding a mark by the use of the implement 7 for making recess used for embedding sealably a mark. A time required for such working is slight and not so much labor is required therefor.

The head 8 may be prepared from any material such as metal, synthetic resin, ceramics, wood, bamboo and the like.

After defining a recess on a wax pattern as a groove for holding a mark, a heat-curing resin is poured into, a gap of the wax pattern and heated. In the artificial gingival section 3 of the resin cured by heating, the groove 5 for holding a mark may be formed at a desired site. The optimal site at which the groove 5 for holding a mark is to be defined resides in the artificial gingival section 3 in the vicinity of the artificial molar tooth 4 on a cheek side where the resin layer is the thickest from the viewpoints of workability, and possible damage of the denture due to occlusal force or external force. In this respect, however, any site, i.e., anywhere in the resin layer of a plate 2 of denture or the like section may be selected for defining the groove 5 for holding a mark so far as the site selected has a sufficient thickness for embedding sealably the mark such as a one-chip microprocessor. Accordingly, a site for defining the groove 5 for holding a mark is not particularly limited. Furthermore, it is desirable that a depth of the groove 5 for holding a mark is kept at such a degree where the mark 6 does neither project nor retracts from a level of the resin layer surface in case of embedding sealably the mark 6. According to such arrangement as described above, there is neither fear of inflicting pain on its user as a result of pressing the mucous membrane in the user's cheek with a section where the mark 6 has been embedded and sealed, nor there is malaise even if the section is touched with the user's tongue.

It is also easy to define the above-mentioned groove 5 for holding a mark on a denture which has already been employed by a patient. In this case, a groove-shaped recess is cut on an artificial gingival section having a thicker thickness by means of a cutter for dental use, and a mark such as a one-chip microprocessor contained in the recess may be sealably embedded with the use of a resin used for direct restoration or the like resin.

Although preferable is one-chip microprocessor as the mark used in the present invention, a metallic plate on which user's name has been punched, an alphabetically shaped synthetic resin plate, a star- or an animal-shaped ceramic plate, or any suitable storage means which will be widely used in the future may be sealably embedded in a recess.

While a commercially available one-chip microprocessor for animal use having a size of around 2 mm diameter and 11 mm length may be applied to the present invention, such size is considered to be relatively too large for use in the present invention. Accordingly, it is desirable to develop a novel one-chip microprocessor used exclusively for dental field in case of practicing the present invention. As a matter of course, the smaller size of such one-chip microprocessor results in the better result in the invention. In this respect, storage capacity of information may be adjusted for miniaturization of one-chip microprocessor to be 15-digit or less according to ISO standard.

When it is arranged in such that owner's name, e.g., Hisashi Kishigami or his initials, e.g., H. K. of a denture can be read together with number of several digit by a reader, management for dentures, identifying work of dentures after having been washed, or the like working in dental office become much more accelerated.

In case of fabricating a denture according to the present invention, it is preferable for embedding sealably a mark to use a resin for direct restoration comprising methyl methacrylate as the major component such as "REPAIRSIN" (trade name) manufactured by K.K. G. C. Dental Products. A mixture of liquid (monomer) and powder (polymer) of "REPAIRSIN" is applied to a one-chip microprocessor contained in a groove-shaped recess 5 in accordance with a conventional brush-on technique. As a result, the mixture sets at ordinary temperatures after lapse of 7 to 8 minutes, so that the one-chip microprocessor can be positively embedded and sealed in a resin layer of an artificial gingival section or the like. Since the resin for direct restoration used adheres perfectly to a heat-curing resin used for molding the artificial gingival section, there is no fear of slipping the mark embedded and sealed from the recess.

Alternatively, a photo-polymerizing resin such as "UNIFAST" (trade name) manufactured by K.K. G. C. Dental Products which is cured with visible rays may be employed for embedding sealably a mark. In this case, a one-chip microprocessor contained in a groove-shaped recess is covered with an admixture of powder and liquid of "UNIFAST", and then, when visible rays are projected on the groove-shaped recess thus covered by the use of a device for irradiating light rays, the photo-polymerizing resin sets at ordinary temperatures after lapse of several minutes without accompanying any thermal treatment.

It is preferred to prepare a transparent portion for embedding and sealing a mark, or the portion having a different color from that of an artificial gingival section. As a result of such modification, the portion where a mark has been embedded and sealed can be recognized at a glance, whereby an operator can allow quickly a reader to come near the mark of one-chip microprocessor to read a number registered. Thus, such reading work for identification becomes easier, and it results in a shorter period of time for working required for identifying dentures.

The present invention may not only be applied to denture, but also any oral artificial product comprising a resin layer such as orthodontic appliance.

A manner of practice according to the present invention will be described hereinafter in conjunction with the accompanying drawings.

In FIGS. 1 and 2, a groove-shaped recess 5 for holding a mark 6 such as a one-chip microprocessor to sealably embed the same therein is defined on an artificial gingival section 3 supported by a plate 2 of a denture 1 on either side of patient's cheek. In usual denture 1, since a resin layer in the vicinity of an artificial molar tooth implanted in the artificial gingival section 3 is the thickest, so that the mark 6 can be positively embedded sealably in the resin layer with a sufficient room, even if the mark is a commercially available one-chip microprocessor for animal use.

In case of embedding sealably the mark 6, liquid (monomer) of a direct resin for restoration is first applied into the groove-shaped recess 5 for holding mark, thereafter, the mark 6 is forcibly inserted in the groove-shaped recess 5 as shown by the arrow A in FIG. 2, and then, the surface of the mark 6 is also coated with the monomer liquid. Then, the tip of a brush is moistened with the monomer liquid, and the tip of the brush thus moistened is allowed to be in contact with a powdered polymer, and a gap defined between the artificial gingival section 3 and the mark 6 is filled with the powder deposited on the tip of the brush, and at the same time, the surface of the mark 6 is also covered with the powder in accordance with a conventional brush-on procedure. Within a period-of several minutes, the liquid begins to polymerize together with the powder, so that such deposition of a mixture of the liquid and the powder is repeated further several times according to the brush-on technique. Finally, the mixture is deposited at a degree wherein the level thereof is slightly higher than the surface of the artificial gingival section 3, and is covered with cellophane, silver foil and the like to allow the same to stand until the resin is set. The curing reaction is completed at ordinary temperatures after the elapse of about seven minutes. After curing, the resulting product is immersed in warm water of about 70° C. for around 20 minutes, and then, the portion under which the mark has been embedded and sealed is smoothed with a grinder, whereby troubles in feeling of tongue in a denture's user may be avoided.

The one-chip microprocessor used for experiments in the course of the development for the invention is "LIFECHIP" (trade name) imported from the Destron-Fearing Corporation in the U.S.A. and sold by Dai-nippon Seiyaku K.K. in Japan, and the one-chip microprocessor has a cylindrical shape of 2 mm diameter and 11 mm length. The one-chip microprocessor is covered by a plastic cap for avoiding intracorporeal movement, so that it is served for experiments after removing the cap. As a result of experiments, such one-chip microprocessor embedded and sealed in a denture functioned normally, so that when a hand-held reader was allowed to come near the portion under which the one-chip microprocessor had been embedded and sealed within a distance of 5 cm or shorter therefrom and emitted inquiry signal, response signal responded instantly from the one-chip microprocessor, whereby a number of 15-digit was displayed on a display of the reader. Thus, such registered number belonging to a denture of its owner can be positively read irrespective of a position of the portion under which a one-chip microprocessor has been embedded and sealed, even when it is any site in the artificial gingival section of the denture. In this case, however, since it is troublesome to frequently turn on such hand-held reader, every dentures may be allowed to come near the antenna of a stationary reader one by one in the case where a number of dentures must be identified continuously.

FIG. 3 is an embodiment of an implement 7 for making recess used for sealably embedding a mark required for fabricating a denture according to the present invention. In the beginning of experiments, the present inventor picked up a one-chip microprocessor, and was allowed to be forcibly in direct contact with a wax pattern thereby defining a recess thereon. However, this procedure is somewhat troublesome, and it was difficult to make a recess having a suitable contour thereof. Before long, an implement to make a recess for holding one-chip microprocessor is prepared by the inventor himself. After repeating experiments, a head 8 was utilized in place of one-chip microprocessor. Finally, the head 8 is fixed on grip 9, and further it has been found by the inventor that a contour of the head 8 having a trapezoidal section is most desirable. More specifically, a head 8 having such trapezoidal section is employed to define a recess upon a wax pattern by forcibly pressing the head thereon, and then, when the head 8 is removed from the wax pattern, edges of the recess of the wax pattern are not damaged, but a clear contour of a groove-shaped recess 5 for holding a mark can be defined on the wax pattern because of the trapezoidal section.

In the implement 7 for making a recess used for sealably embedding a mark shown in FIG. 3, the head 8 has such dimensions that a longer side and a shorter side are 12 mm and 2 mm in the top surface of the trapezoidal section which correspond substantially to those of the above described one-chip microprocessor, respectively, as well as a longer side and a shorter side are 12 mm and 3 mm in the bottom surface thereof, and a height thereof is about 3 mm. A grip 9 is secured to the bottom surface of the head 8 at the central portion thereof. Any contour of the grip 9 may be applied, and a size of which may be the one being sufficient for holding the same with a hand.

A prototype of the head 8 was made from hard box-wood material. As a result, it was very convenient to make a recess for holding a mark, because the head 8 of box-wood is not excessively heated in case of warming the same in hot water, so that there is no fear of excessively melting a wax pattern.

However, box-wood is expensive and much labor is required for working box-wood material. Accordingly, the head 8 may be made from a synthetic resin material coated with Teflon in such that wax does not stick to the head 8.

The present invention which has been practiced in the manner as described above exhibits the following advantages. Namely, a mark has been embedded and sealed after defining a recess for holding the same on an artificial tooth implanted in a denture according to a conventional technique, while a mark is embedded and sealed in the resin layer having a thicker thickness of artificial gingival section in a denture capable of identifying its owner according to the present invention. Thus, there is no fear of deteriorating strength of artificial tooth, so that a denture according to the present invention can be applied for positively confirming identities of old people in practical use.

Furthermore, since a one-chip microprocessor is employed as a mark to be sealably embedded and a registered number of the one-chip microprocessor is read by a reader, an owner of a dentures according to the present invention can be identified easily and positively. Accordingly, when an Alzheimer's patient with poriomania is kept from harm in another place, or when an old man who is in indistinct consciousness as a result of a traffic accident, his (or her) identity can be immediately specified so far as the old man puts on a denture with a one-chip microprocessor according to the invention.

Moreover, in a dental office where a number of dentures must be managed, when a registered number of a one-chip microprocessor embedded and sealed in each denture is checked against records contained in clinical recording or computer, a date on which each denture was fabricated and the like information can be instantly specified.

In senior citizens' home where a number of dentures must be collectively washed in every meals, each denture after having been washed can be returned to its owner without accompanying any mistake by reading successively a registered number of each denture by means of a reader. Thus, the staff for washing dentures can perform quickly and easily their working for treating such dentures after finishing every meals as a result or being released from conventional troublesome reading of carved characters.

Since a direct resin for restoration is used as a resin for embedding sealably a mark in case of fabricating a denture capable of identifying its owner according to the present invention, a one-chip microprocessor can be embedded sealably in a resin layer of the denture without heating the one-chip microprocessor having no heat-resisting properties.

Furthermore, when an implement for making a recess for sealably embedding a mark is employed, a groove-shaped recess having the substantially same dimension as that of a one-chip microprocessor can be very easily and positively defined on a wax pattern without damaging the same. Thus, a one-chip microprocessor may be tightly held in the groove-shaped recess defined on the resin layer of a denture, and it can be embedded sealably with the use of a direct resin for restoration or the like.

It will be appreciated by those of ordinary skill in the art that the present invention can be embodied in other specific forms without departing from the spirit or essential characteristics thereof.

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method of embedding a mark in a plate denture comprising the steps of:

(a) pressing an implement into a surface of a wax pattern so as to form a recess therein;

(b) pouring a heat-curing resin into the wax pattern to form a plate denture having a recess therein;

(c) inserting a mark into the recess of the plate denture, (d) covering the mark with a resin.

* * * * *